(12) United States Patent
Gill et al.

(10) Patent No.: US 6,394,966 B1
(45) Date of Patent: May 28, 2002

(54) APPARATUS AND METHOD FOR REMOVING CELLS FROM AN ENDOCERVICAL BRUSH IN A LIQUID-BASED PAP TEST SYSTEM

(75) Inventors: Gary W. Gill; James A. Snyder, both of Indianapolis, IN (US)

(73) Assignee: Diagnostic Cytology Laboratories, Inc., Indianapolis, IN (US)

( * ) Notice: Subject to any disclaimer, the term of this patent is extended or adjusted under 35 U.S.C. 154(b) by 59 days.

(21) Appl. No.: 09/658,109

(22) Filed: Sep. 8, 2000

(51) Int. Cl.[7] ............................................. A61B 10/00
(52) U.S. Cl. ...................................... 600/569; 600/570
(58) Field of Search .................... 600/562, 569, 600/570; 606/119, 160

(56) References Cited

U.S. PATENT DOCUMENTS

| | | | |
|---|---|---|---|
| 3,945,372 A | * | 3/1976 | Milan et al. .............. 600/569 |
| 4,054,127 A | * | 10/1977 | Milan et al. .............. 600/569 |
| 4,127,113 A | | 11/1978 | Nollan |
| 4,620,548 A | | 11/1986 | Hasselbrack |
| 4,759,376 A | | 7/1988 | Stormby |
| 5,184,626 A | | 2/1993 | Hicken |
| 5,191,899 A | | 3/1993 | Strickland et al. |
| 5,259,391 A | | 11/1993 | Altshuler et al. |
| 5,357,977 A | | 10/1994 | Michels |
| 5,370,128 A | | 12/1994 | Wainwright |
| 5,422,273 A | | 6/1995 | Garrison et al. |
| 5,456,265 A | | 10/1995 | Yim |
| 5,471,994 A | | 12/1995 | Guirguis |
| 5,533,517 A | | 7/1996 | Michels |
| 5,900,374 A | | 5/1999 | Otto-Nagels |

OTHER PUBLICATIONS

"Current understanding and management of glandular lesions of the cervix," Contemporary OB/GYN, pp. 4–18 (Apr. 15, 2000 Supplement).

Kohlberger, Petra D., M.D., et al, "Comparative Evaluation of Seven Cell Collection Devices for Cervical Smears," Acta Cytologica, vol. 43, No. 6, pp. 1023–1026 (Nov.–Dec., 1999).

* cited by examiner

*Primary Examiner*—Kevin Shaver
*Assistant Examiner*—Brian Szmal
(74) *Attorney, Agent, or Firm*—James P. Davidson

(57) ABSTRACT

A device for collecting cervicovaginal cells, including a first end portion for contacting an ectocervical region and obtaining a sampling of cells therefrom, a second end portion opposite the first end portion, and an elongated middle portion connecting the first and second end portions. A region is formed on the device that provides a designated edge against which an endocervical brush is able to be rubbed for harvesting of cells from the endocervical brush in a vial of preservative.

37 Claims, 3 Drawing Sheets

APPARATUS AND METHOD FOR REMOVING CELLS FROM AN ENDOCERVICAL BRUSH IN A LIQUID-BASED PAP TEST SYSTEM

BACKGROUND OF THE INVENTION

1. Field of the Invention

The present invention relates generally to a liquid-based Pap test and, more particularly, to an apparatus and method for removing cells from an endocervical brush utilized to obtain a specimen for testing.

2. Description of Related Art

Detection and diagnosis of a variety of diseases, such as cancer, often involves the collection and microscopic examination of a cell sample. Such cell samples, as in the Papanicolaou ("Pap") test, are typically collected from a patient with a type of cytology sampling device. Such sampling devices include various types of brushes (e.g., the Cervix-brush made by Rovers of Oss, The Netherlands and the Cytobrush made by Medscand of Malmo, Sweden) and spatulas (e.g., the Szalay spatula made by C.S.M. Graf & Co., of Steinach Switzerland, the Papex spatula made by Hengstberger of Vienna Austria, and the WrGKK spatula utilized by the main social security in Vienna, Austria), as well as cotton swabs and loop-type devices.

In the case of brush type sampling devices, the cell samples must be transferred after collection from the bristles of the brush to a glass slide that allows for the examination of the cells. In order to obtain the best diagnosis, it is imperative that the cell samples be completely and accurately transferred from the brush to the testing medium. Not only can this affect the diagnosis, but women may be reluctant to have the procedure repeated when an inadequate sample is taken. It will be understood that an inadequate sample may include the instance where no abnormal cells are transferred to the glass slide, which results in false negatives that go unnoticed.

In particular, it will be appreciated that a liquid-based Pap test is growing in use by many doctors and labs. This involves the cell sample being transferred from the brush to a fixative or preservative within a vial or other container. One example of an FDA-approved liquid based preparation product is the ThinPrep® Pap Test™ ("TPPT") made by Cytyc Corporation of Boxborough, Massachusetts. As seen in the protocol for the TPPT, which is described in a ThinPrep® Pap Test Quick Reference Guide (1997), the brush is rotated vigorously while being pushed against the vial wall in order to release the cell sample in the solution. It will be appreciated, however, that pushing the cytology brush against the vial wall can have the detrimental effect of compacting the cell sample to the bristles. Additionally, the brush may not even touch the vial wall if the shaft of the brush is held in a certain way.

While the protocol set forth in the TPPT has been successful in gaining approval from the Food and Drug Administration. it has been found to be very operator dependent and results could be improved if a greater release of the cell sample from the brush is accomplished. One attempt at enhancing the transfer of a cell sample from a brush is disclosed in U.S. Pat. No. 5,422,273 to Garrison et al. As seen therein, the vial containing the fixative solution is constructed so as to include a plurality of fins therein. In this way, a surface is available against which the brush may be agitated or scraped when the brush is rotated. Although this approach may assist in dislodging cell sample from the brush bristles, the vial utilizing such fins is not without disadvantages. Most importantly, it will be recognized that the vial containing the fixative/cell sample undergoes a filtering process in a device known as a ThinPrep processor specially suited for such purpose and described in a manual entitled "ThinPrep® 2000 Operator Manual." Since the vial disclosed in the '273 patent does not have smooth cylindrical walls and is not sized to accept the filter, it could not be utilized in the ThinPrep processor.

Accordingly, it is a primary object of the present invention to provide an apparatus and method that improves the harvesting of endocervical cells for testing in a liquid-based Pap test.

It is another object of the present invention to provide an apparatus and method that increases the number of cells obtained from an endocervical brush for testing in a liquid-based Pap test, as well as minimize the residual brush specimen.

It is still another object of the present invention to provide an apparatus and method with respect to a liquid-based Pap test that obtains more accurate results, reduces screening time by providing increased numbers of abnormal cells that are more readily located, and reduces the need for rescreening and retesting.

Yet another object of the present invention is to provide an apparatus and method that facilitates an increase in the detection rates for AGUS/AIS cases and squamous lesions in a liquid-based Pap test.

Another object of the present invention is to provide an apparatus and method that increases the archived volume of preserved cell suspension in a liquid-based Pap test for ancillary STD testing.

Still another object of the present invention is to provide an apparatus and method that facilitates harvesting of cells for a liquid-based Pap test so as to be less operator dependent.

These objects and other features of the present invention will become more readily apparent upon reference to the following description when taken in conjunction with the following drawings.

SUMMARY OF THE INVENTION

In accordance with a first aspect of the present invention, a device for collecting cervicovaginal cells is disclosed as including a first end portion for contacting an ectocervical region and obtaining a sampling of cells therefrom, a second end portion opposite the first end portion, and an elongated middle portion connecting the first and second end portions. A region is formed on the device that provides a designated edge against which an endocervical brush is able to be rubbed for harvesting of cells from the endocervical brush in a vial of preservative.

In accordance with a second aspect of the present invention, a device for assisting in the removal of transformation zone cells from an endocervical brush in a liquid-based system is disclosed as including a first end portion, a second end portion, and an elongated middle portion connecting the first and second end portions. A region is formed on the device that provides a designated edge against which the endocervical brush is able to be rubbed for harvesting of endocervical cells from the endocervical brush in a vial of preservative.

In accordance with a third aspect of the present invention. a method of harvesting cells from an endocervical brush in a liquid-based system is disclosed as including the steps of providing a vial at least partially filled with a designated preservative, placing a device in the vial so that a portion thereof is submerged in the designated preservative, where the device has a region formed therein that provides a designated edge, positioning the endocervical brush within the vial, orienting the endocervical brush with respect to the device, and moving the endocervical brush so that bristles thereof rub back and forth against the designated edge of the device.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
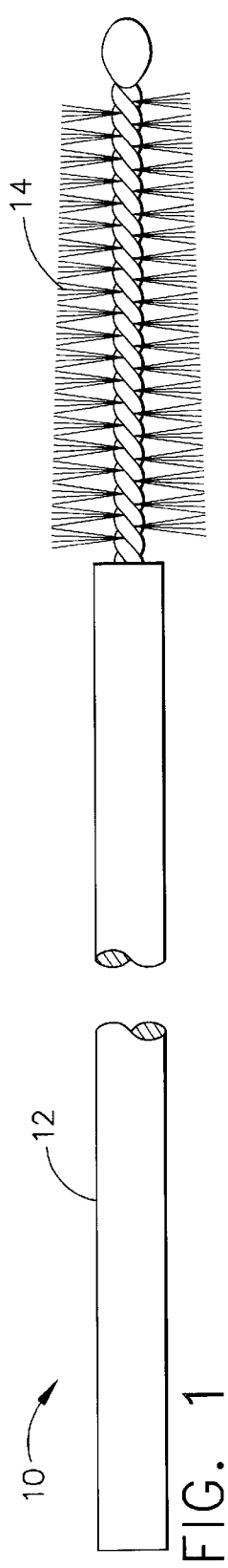
FIG. 1 is a longitudinal view of a cytology brush utilized to obtain endocervical cell samples.

Referring now to the drawings in detail, wherein identical numerals indicate the same elements throughout the figures, FIG. 1 depicts a cytology brush 10 utilized in obtaining a cell sample from the endocervical region of a woman. Although described in greater detail herein, an exemplary brush is disclosed in U.S. Pat. No. 4,759,376 to Stormby. As seen therein, brush 10 includes an elongated handle shaft 12 having opposite ends and an elongated brush portion 14 attached at one end of and concentrically with handle shaft 12. It will be further seen that brush portion 14 is preferably substantially cone-shaped so that the flexible bristles thereof have a diameter range that increases as they are positioned toward the middle of handle shaft 12.

Figure 5:
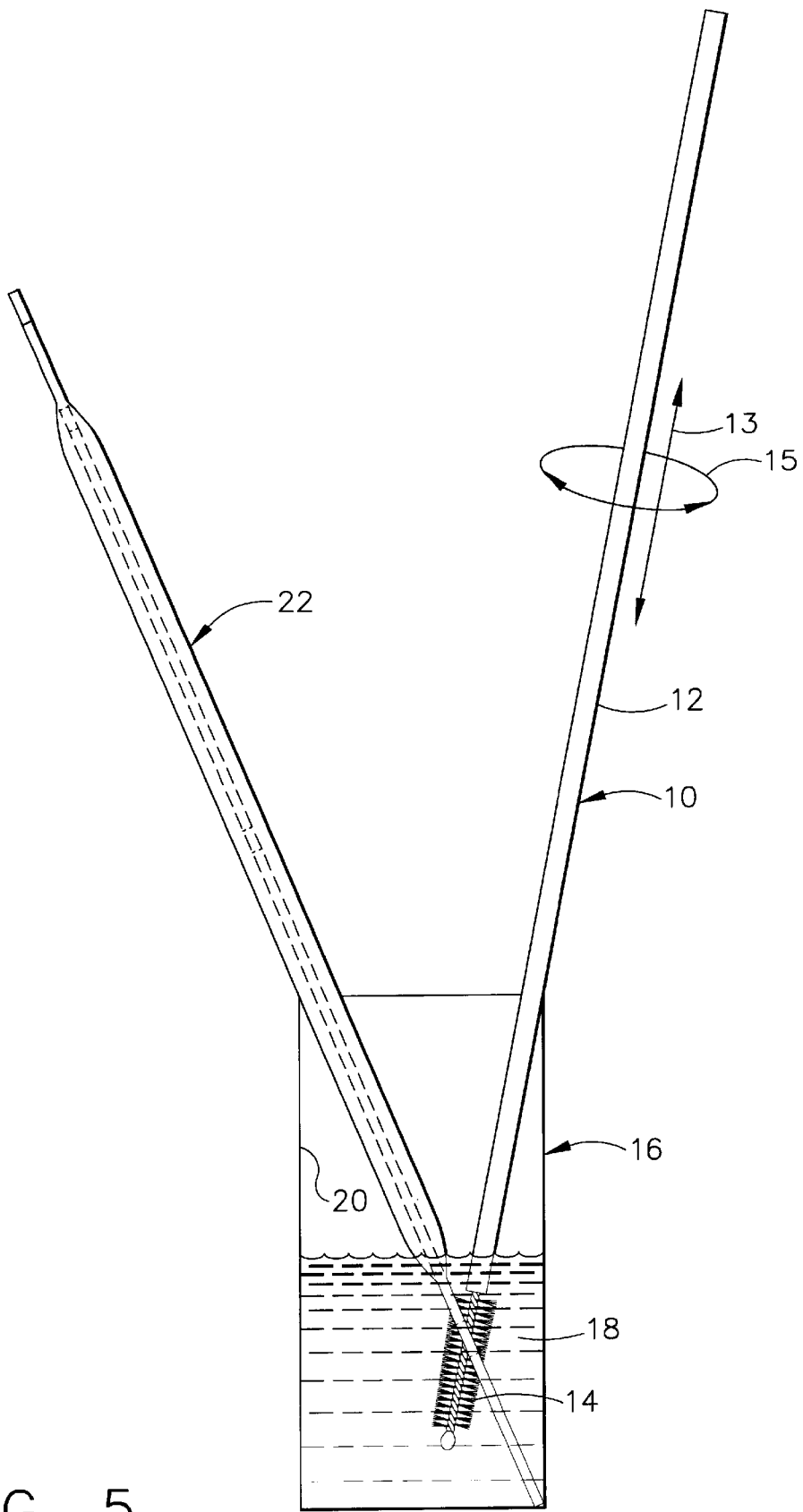
FIG. 5 is a side view of the cytology brush and spatula depicted in FIGS. 1 and 2 being positioned within a vial containing a preservative, wherein the brush is moved in relation to the spatula in accordance with the present invention; and, FIG. 6 is a longitudinal view of the spatula depicted in FIGS. 2 and 3, wherein the spatula has been modified in accordance with an alternative embodiment of the present invention.

After brush 10 obtains the desired cell sample, it is then necessary according to a liquid-based Pap test (e.g., the ThinPrep® Pap Test™) to transfer such sample to a vial 16 containing a predetermined amount of preservative or fixative 18 therein (see FIG. 5). In this way, the sample is able to be processed by a ThinPrep® processor so as to produce a glass slide for analysis according to the well known Papanicolaou technique. Rather then merely swirl brush 10 within preservative 18 or push the bristles of brush portion 14 against a side wall 20 of vial 16 as indicated under the current TPPT protocol, the present invention involves utilizing a device 22 in conjunction therewith to improve removal of the cell sample into preservative 18.

Figure 2:
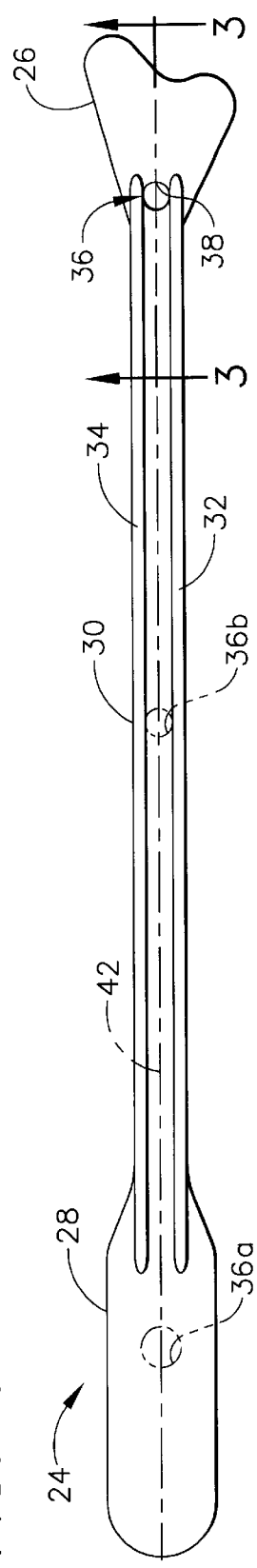
FIG. 2 is a longitudinal view of a spatula utilized to obtain cervicovaginal cell samples, wherein the spatula has been modified in accordance with the present invention.

Accordingly, the present invention discloses in a preferred embodiment an improvement to a device 22 utilized for removing or collecting cervicovaginal cells that is performed in conjunction with the endocervical cell collection by brush 10 and already exposed to the endocervical region. Several types of such devices 22 are employed for such purpose and include various types of spatulas, brushes, brooms and the like. While a spatula is depicted in FIGS. 2–4 for the purposes of discussion, it will be appreciated that any device 22 containing the essential features described may be utilized and falls within the scope of the invention.

With respect to FIGS. 2–4 and 6, it will be seen that an Ayre-type spatula 24 is depicted that includes a first end portion 26 for contacting an ectocervical region and obtaining a sampling of cells therefrom, a second end portion 28 for grasping and operating spatula 24, and an elongated middle portion 30 connecting first and second end portions 26 and 28, respectively. Spatula 24 is preferably made of a plastic material and includes a pair of ribs 32 and 34 in parallel orientation extending along and raised from at least one side of middle portion 30 to strengthen spatula 24. In accordance with the present invention, a region is formed on spatula 24 that provides a designated edge against which brush 10 is able to be agitated or rubbed for enhanced harvesting of endocervical cells.

More specifically, such region is preferably an opening 36 formed within spatula 24 which is sized so that brush portion 14 of brush 10 rubs against an edge 38 defining such opening 36 when it is moved back and forth therethrough. Although opening 36 may be positioned within first end portion 26, second end portion 28, or middle portion 30 of spatula 24 (see the alternative openings 36a and 36b in phantom in FIG. 2), it is preferred that it be located so as to take into account the depth of preservative 18 in vial 16 whereby brush portion 14 of brush 10 is able to remain submerged in such preservative 18 during cell removal. Accordingly, a preferred location for opening 36 is depicted in FIGS. 2 and 3 as being at a transition area between first end portion 26 and middle portion 30. Not only does this enable handling of spatula 24 at the same end portion 28 as during collection of cells from the ectocervical region, but also permits ribs 32 and 34 to facilitate alignment and orientation of brush portion 14 through opening 36.

Figure 3:
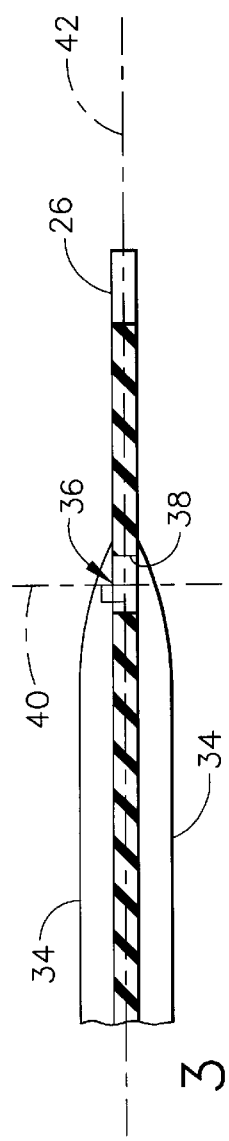
FIG. 3 is an enlarged, partial cross-sectional view of the spatula depicted in FIG. 2, where the opening therein is formed so that an axis through a centerpoint of such opening is substantially perpendicular to a longitudinal axis through such spatula.
Figure 4:
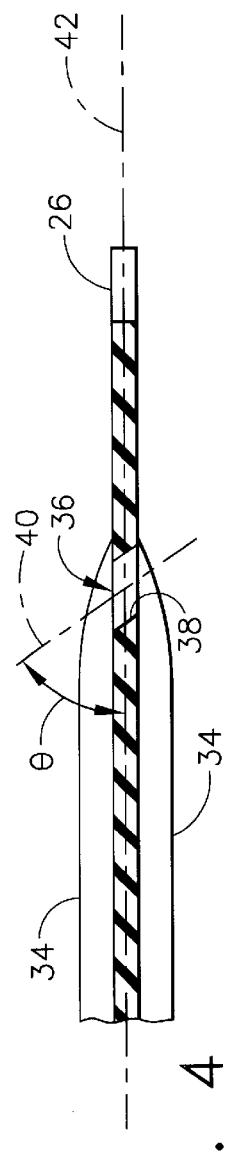
FIG. 4 is an enlarged, partial cross-sectional view of the spatula depicted in FIG. 2, where the opening therein is formed so that an axis through a centerpoint of such opening is oriented at an acute angle to a longitudinal axis through such spatula.

It will be seen from FIG. 3 that an axis 40 through the center of opening 36 is oriented substantially orthogonal to a longitudinal axis 42 through spatula 24, but may be formed therein at an acute angle θ to such axis 42 (see FIG. 4) so as to further ease insertion of brush portion 14 therethrough. Rather than angle opening 36 in spatula 24, however, it will be appreciated that middle portion 30 thereof may itself be non-linear or non-linear with respect to first end portion 26 to better accommodate insertion through opening 36.

Further, opening 36 is preferably substantially circular or substantially elliptical in shape. In either case, opening 36 is sized so as to assure interference with all sizes of bristles comprising brush portion 14. Thus, opening 36 will preferably have a diameter in a range of approximately 0.25–0.75 the length of bristles when substantially circular, which will typically be 0.125–0.25 of an inch. When opening 36 is substantially elliptical, the major axis will preferably be substantially parallel to a centerline through spatula 24. Thus, the major axis will be either substantially parallel to longitudinal axis 42 or at an acute angle θ thereto as indicated hereinabove. It will also be understood that opening 36 may be other shapes so long as it is able to perform the intended function of providing an edge 38 or a plurality of discrete edges against which brush portion 14 may be agitated or rubbed.

Figure 6:
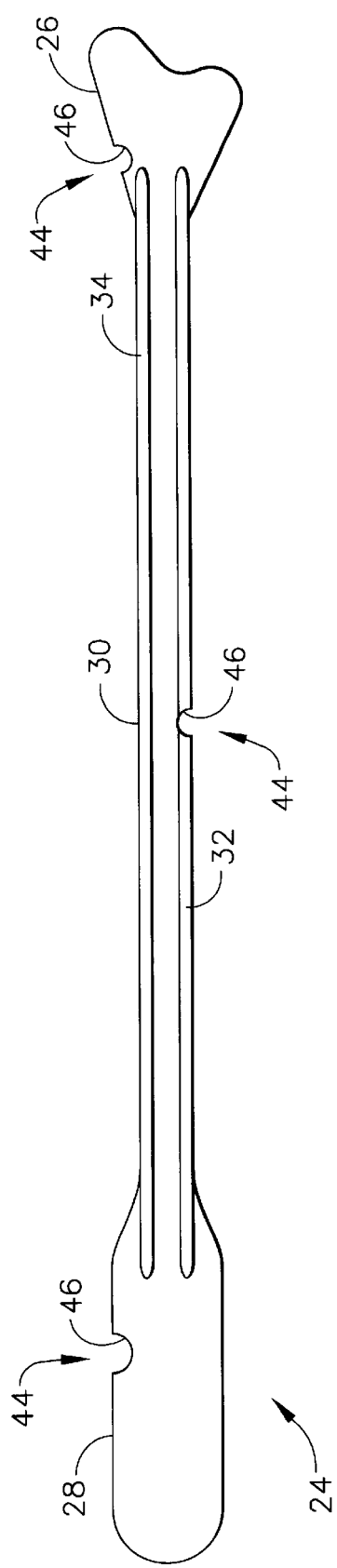

In this regard, it is also contemplated by the present invention that a region may be formed along a periphery of device 22 to provide the designated edge. While this necessarily prevents the designated edge from completely encircling brush portion 14 entirely, it can still perform the intended function since brush 10 not only is moved back and forth thereagainst in a single axis of motion, but preferably rotated (or twisted) simultaneously (note arrows 13 and 15, respectively in FIG. 5). Such motion allows all of brush portion 14 to be rubbed against such designated edge by simply reorienting brush 10 as necessary. Such an alternative design is depicted in FIG. 6, for example, as a curved area 44 having an edge 46. This curved area 44 may likewise be positioned anywhere along the periphery of first end portion 26, second end portion 28, or middle portion 30 and take on any desired shape, but preferably is located at the transition of first and middle portions 26 and 30, respectively. The principle consideration is that curved area 44 be configured and sized so that substantially all bristles of brush portion 14 can be rubbed thereagainst. In the case where curved area 44 is substantially semi-circular in shape, it will preferably have a diameter in a range of approximately 0.25–0.75 the length of the brush portion bristles (i.e., approximately 0.125–0.75 of an inch).

In light of the foregoing description, it will be appreciated that an improved method for harvesting cells from endocervical brush 10 in a liquid-based system is realized by performing the following steps: (1) providing a vial 16 at least partially filled with a preservative 18; (2) placing a device 22 in vial 16 so that a portion thereof is submerged in preservative 18, wherein device 22 has a region formed therein which provides a designated edge; (3) positioning endocervical brush 10 within vial 16 so as to be aligned with such region of device 22; and, (4) moving endocervical brush 10 several times so that the bristles of brush portion 14 rub back and forth against a designated edge of device 22 (see arrow 13 in FIG. 5). This method is further enhanced by rotating endocervical brush 10 as it is moved through the region, as represented by arrow 15 in FIG. 5. Depending on the orientation of the region, endocervical brush 10 is aligned either substantially orthogonal to device 22 or at an acute angle thereto. It will further be understood that vial 16 will preferably be stabilized during the above steps so as to better enable the technique of the present invention to be practiced.

Having shown and described the preferred embodiment of the present invention, further adaptations of the device and method in which it is utilized with an endocervical brush can be accomplished by appropriate modifications by one of ordinary skill in the art without departing from the scope of the invention.

What is claimed is:

1. A device for collecting cervicovaginal cells, comprising:
   (a) a first end portion for contacting an ectocervical region and obtaining a sampling of cells therefrom;
   (b) a second end portion opposite said first end portion; and
   (c) an elongated middle portion connecting said first and second end portions;
wherein a region is formed on said device that provides a designated edge against which an endocervical brush is able to be rubbed for harvesting of cells from said endocervical brush in a vial of preservative.

2. The device of claim 1, wherein said device is a spatula.

3. The device of claim 1, wherein said device is a broom.

4. The device of claim 1, wherein said region is positioned at said first end portion.

5. The device of claim 1, wherein said region is positioned at said second end portion.

6. The device of claim 1, wherein said region is positioned at said middle portion.

7. The device of claim 1, wherein said region is an opening formed in said device.

8. The device of claim 7, wherein said opening is formed in said first end portion.

9. The device of claim 7, wherein said opening is formed in said middle portion.

10. The device of claim 7, wherein said opening is formed in said second end portion.

11. The device of claim 7, wherein said opening is sized so that bristles of said endocervical brush rub against an edge defining said opening.

12. The device of claim 7, wherein said opening is oriented substantially orthogonal to a longitudinal plane extending through said device.

13. The device of claim 7, wherein said opening is oriented at an acute angle to a longitudinal plane extending through said device.

14. The device of claim 7, wherein said opening is substantially circular in shape.

15. The device of claim 7, wherein said opening is substantially elliptical in shape.

16. The device of claim 15, wherein a major axis of said opening is oriented substantially parallel to a centerline extending through said device.

17. The device of claim 15, wherein a major axis of said opening is oriented at an angle to a centerline extending through said device.

18. The device of claim 7, wherein said opening has a diameter of approximately 0.125–0.25 of an inch.

19. The device of claim 1, wherein said region is a curved edge located about the periphery of said device.

20. The device of claim 19, wherein said curved edge is located about the periphery of said second end portion.

21. The device of claim 19, wherein said curved edge is located about the periphery of said middle portion.

22. The device of claim 19, wherein said curved edge is located about the periphery of said first end portion.

23. The device of claim 1, wherein said region is positioned on said device so as to remain submerged within said preservative in said vial.

24. The device of claim 7, wherein said opening is sized so that a radius thereof is approximately 0.25–0.75 the length of said endocervical brush bristles.

25. The device of claim 19, wherein said curved edge is sized so that bristles of said endocervical brush rub against said curved edge.

26. The device of claim 19, wherein said curved edge is sized so that a radius thereof is approximately 0.25–0.75 the length of said endocervical brush bristles.

27. A device for assisting in the removal of transformation zone cells from an endocervical brush in a liquid-based system, comprising:
   (a) a first end portion;
   (b) a second end portion; and
   (c) an elongated middle portion connecting said first and second end portions;
wherein a region is formed on said device that provides a designated edge against which said endocervical brush is able to be rubbed for harvesting of endocervical cells from said endocervical brush in a vial of preservative.

28. A method of harvesting cells from an endocervical brush in a liquid-based system, comprising the following steps:
 (a) providing a vial at least partially filled with a designated preservative;
 (b) placing a device in said vial so that a portion thereof is submerged in said designated preservative, said device having a region formed therein which provides a designated edge;
 (c) positioning said endocervical brush within said vial;
 (d) orienting said endocervical brush with respect to said device; and,
 (e) moving said endocervical brush so that bristles thereof rub back and forth against said designated edge of said device.

29. The method of claim 28, said moving step further comprising rotating said endocervical brush as said bristles rub against said designated edge of said device.

30. The method of claim 28, further comprising the step of stabilizing said vial in a base.

31. The method of claim 28, wherein said bristles of said endocervical brush are maintained within said designated preservative in said vial during said moving step.

32. The method of claim 28, wherein said designated edge of said device is formed by an opening therein.

33. The method of claim 28, wherein said designated edge of said device is formed by a curved edge located along a periphery thereof.

34. The method of claim 28, wherein said device is an ectocervical collection device.

35. The method of claim 32, wherein said opening is sized so that a radius thereof is less than the length of said endocervical brush bristles.

36. The method of claim 33, wherein said curved edge is sized so that a radius thereof is less than the length of said endocervical brush bristles.

37. The method of claim 28, wherein said endocervical brush is oriented substantially orthogonally to said designated edge during said moving step.

* * * * *

UNITED STATES PATENT AND TRADEMARK OFFICE
CERTIFICATE OF CORRECTION

PATENT NO.     : 6,394,966 B1
DATED          : May 28, 2002
INVENTOR(S)    : Gary W. Gill et al.

It is certified that error appears in the above-identified patent and that said Letters Patent is hereby corrected as shown below:

Column 5,
Line 60, -- adapted -- should be added after "portion" and before "for"

Signed and Sealed this

Twenty-second Day of October, 2002

Attest:

Attesting Officer

JAMES E. ROGAN
Director of the United States Patent and Trademark Office